United States Patent
Young et al.

(10) Patent No.: US 6,610,268 B1
(45) Date of Patent: Aug. 26, 2003

(54) METHOD FOR THE MICROBIOLOGICAL PRODUCTION OF SULFURIC ACID

(75) Inventors: Tom L. Young, Tucson, AZ (US);
Michael G. Greene, Tucson, AZ (US);
Dennis R. Rice, Oracle, AZ (US);
Kelly L. Karlage, Tucson, AZ (US);
Sean P. Premeau, Tucson, AZ (US);
Janet M. Cassells, Tucson, AZ (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/546,997

(22) Filed: Apr. 12, 2000

Related U.S. Application Data

(60) Provisional application No. 60/128,796, filed on Apr. 12, 1999.

(51) Int. Cl.$^7$ .............................................. C01B 17/76
(52) U.S. Cl. ........................................................ 423/522
(58) Field of Search ........................................ 423/522

(56) References Cited

U.S. PATENT DOCUMENTS

| | | | |
|---|---|---|---|
| 5,366,891 A | | 11/1994 | Premuzic et al. |
| 5,753,201 A | * | 5/1998 | Lin |
| 5,914,441 A | | 6/1999 | Hunter et al. |

FOREIGN PATENT DOCUMENTS

| | | | |
|---|---|---|---|
| DE | 2557008 A | 12/1975 | |

OTHER PUBLICATIONS

R. Tichý et al., "Possibilities for Using Biologically–Produced Sulphur for Cultivation of Thiobacilli With Respect to Bioleaching Processes", *Bioresource Technology* 48 (1994) pp. 221–227.

C. Cerruti et al., "Bio–dissolution of spent nickel–cadmium batteries using *Thiobacillus ferrooxidans*", *Journal of Biotechnology* 62 (1998) pp. 209–219.

G. Curutchet et al., "Combined Degradation of Covellite by *Thiooxiodans* and *Thiobacillus Ferrooxidans*", *Biotechnology Letters*, vol. 18 No. 12 (Dec. 1996) pp. 1471–1476.

C. Brissette et al., "Bacterial Leaching of Cadmium Sulphide", *The Canadian Mining and Metallurgical (CIM)* Oct., 1971, pp. 85–88.

R. Tichý et al., "Oxidation of Biologically–Produced Sulphur in a Continuous Mixed–Suspension reactor", *Wat. Res.*, vol. 32, No. 3, (1998), pp. 701–710.

A. Pich Otero, et al., "Action of *Thiobacillus thiooxidans* on Sulphur in the Presence of a Surfactant Agent and its Application in the Indirect Dissolution of Phosphorus", *Process Biochemistry*, vol. 30, No. 8, (1995) pp. 747–750.

"Bio–dissolution of spent–nickel–cadmium batteries using Thiobacillus ferrooxidans", Cerruti et al., J. Biotechnol., 1998, vol. 62, pp. 209–219.

"Combined Degradation of Covellite by Thiobacillus thiooxidans and Thiobacillus ferrooxidans", Curutchet et al., Biotechnology Letters, Dec. 1996, vol. 18, pp. 1473–1476.

\* cited by examiner

*Primary Examiner*—Joseph K. McKane
*Assistant Examiner*—Sonya N. Wright
(74) *Attorney, Agent, or Firm*—McDermott, Will & Emery

(57) ABSTRACT

A process and apparatus for the biological production of sulfuric acid are provided.

20 Claims, 3 Drawing Sheets

METHOD FOR THE MICROBIOLOGICAL PRODUCTION OF SULFURIC ACID

This application claims the benefit of U.S. Provisional Application No. 60/128,796, filed Apr. 12, 1999, the disclosure of which is hereby incorporated by reference.

BACKGROUND OF THE INVENTION

Through its major derivative, sulfuric acid, sulfur ranks as one of the most important elements used as an industrial raw material. It is of prime importance to every sector of the world's industrial and fertilizer complexes. Sulfuric acid production is the major end use for sulfur, and consumption of sulfuric acid has been regarded as one of the best indexes of a nation's industrial development. More Sulfuric acid is produced in the United States every year than any other chemical, nearly 48 million metric tons. The World production of sulfuric acid is over 150 million metric tons per year.

There is a wide range of industrial applications for sulfuric acid. Some examples of these include uses in: phosphorus and nitrogen fertilizers; petroleum refining; mineral leaching, i.e. copper, zinc, nickel and titanium extraction; industrial organic and inorganic chemical production; the processes for manufacturing paints and pigments; the iron, steel and non-ferrous metallurgy industry; the production of rayon and cellulose film; pulp and paper; and water treatment. Because of its desirable properties, sulfuric acid has retained its position as the most universally used mineral acid and the most produced and consumed inorganic chemical, by volume.

Sulfuric acid is typically produced via a catalyzed transformation of sulfur dioxide ($SO_2$) into sulfur trioxide ($SO_3$), followed by the reaction of $SO_3$ with water to form sulfuric acid. Typically, the source of the $SO_2$ is either by the direct burning of elemental sulfur or via base metal smelting (e.g. Copper, Zinc and Lead). Even though the process technologies for both metals based and direct sulfur burning to capture $SO_2$ from release have been greatly improved, these process are still only capturing between 95% to 99% of the emissions. Old technologies based smelters where the emissions regulations are significantly less stringent, are located in remote locations mainly in South America, Southern Africa and China where they have largely been unaffected by mounting environmental pressures. However, even these remotely located smelters will be under increasing pressure in the future to reduce the quantity of noxious emissions. The retrofit would be capital-intensive. Accordingly, it would be advantageous to have a process for producing sulfuric acid which eliminates the hazards to the environment that are associated with the current production of sulfuric acid.

Additionally, operations such as metal leaching often have mines and plants located in remote areas and in countries lacking the infrastructure necessary to handle the extremely dangerous concentrated sulfuric acid. Most leaching operations use aqueous solutions of sulfuric acid that contain less than 20 grams per liter of sulfuric acid. With current technology, sulfuric acid is made in very concentrated form and then shipped to the point of use where it is diluted with water to produce the aqueous solutions used in most leaching operations. Accordingly, it would be advantageous to have a process which permits generation of aqueous sulfuric acid solutions very near the point of use and eliminates the hazards associated with the transport and handling of concentrated sulfuric acid.

As illustrated above, there is a long felt need for a more cost efficient and environmentally friendly process for producing sulfuric acid. The subject invention provides an alternative process for producing sulfuric acid that utilizes commercially available non-hazardous sulfur and/or sulfide ores and/or minerals that allow sufficient solid/liquid/gas transfer for commercial production. The process would be significantly lower in capital cost than either of the current processes and it reduces the environmental impact by nearly eliminating emissions.

The concept of producing sulfuric acid in small-scale submerged reactors utilizing biological means has been discussed in the literature by Cerruti et al., *Bio-dissolution of Spent Nickel-Cadmium Batteries using Thiobacillus Ferroxidans,* Journal of Biotechnology 62, 209–211 (1998); Curutchet et al., *Combined Degradation of Covellite by Thiobacillus Thiooxidans and Thiobacillus Ferrooxidans,* Biotechnol. Lett. 18, 1471–1476 (1996); Tichy et al., *Possibilities for Using Biologically-Produced Sulphur for Cultivation of Thiobacilli with Respect to Bioleaching Processes,* Bioresource Technology 48, 221–227 (1994); Tichy et al., *Oxidation of Biologically-Produced Sulphur in a Continuous Mixed-Suspension Reactor,* Wat. Res. Vol. 32, 701–719 (1998); Otero et al., *Action of Thiobacillus Thiooxidans on Sulphur in the Presence of a Surfactant Agent and its Application in the Indirect Dissolution of Phosphorus,* Process Biochemistry, Vol. 30, 747–750 (1995); and Brissette et al., *Bacterial Leaching of Cadmium Sulphide,* The Canadian Mining and Metallurgical (CIM) Bulletin for October, 1971, 85–88 (1971). However, in these studies the elemental sulfur used was described as powder, flower, crystalline or biological for small laboratory operations. Tichy (1994) indicated that acid production rates using elemental-sulfur flower are too low and industrial applications of this process are doubtful. Accordingly, it would be advantageous to have a process that could generate sulfuric acid through biological means at production rates that are suitable for industrial applications.

SUMMARY OF THE INVENTION

It is an object of this invention to provide a novel process and apparatus for the biological production of sulfuric acid ($H_2SO_4$).

Another object of this invention is to produce a low cost process and apparatus capable of producing sulfuric acid product at production rates suitable for industrial applications.

Another object of this invention is to provide a more environmentally friendly process for producing sulfuric acid than either direct burning of the elemental sulfur or base metal smelting.

Yet another object of this invention is to provide a process for producing sulfuric acid that can be safely and economically located at the point of use for the sulfuric acid; thus, eliminating transportation and handling concerns.

Other objects and advantages will be apparent from the detailed description of the appended claims.

The subject invention pertains to the biological production of sulfuric acid ($H_2SO_4$). In a preferred embodiment, the method of the subject invention involves using oxidizing bacteria or acidophilic fungi to oxidize elemental sulfur or pyrite to form sulfuric acid. In a specific embodiment, the sulfur is treated with water in the presence of sulfur oxidizing microbes. In a specific embodiment, the bioleaching can be performed using the oxidizing bacterium *Thiobacillus Thiooxidans.*

According to one aspect of the invention a process for producing sulfuric acid is provided. The process comprises contacting an aqueous solution with a sulfur material in the form of a pile. The sulfur material is selected from the group consisting of elemental sulfur, sulfur-containing ores, sulfide-containing ores, sulfur-containing minerals, sulfide-containing minerals and combinations thereof. The pile additionally contains acidophilic microbes and, preferably, a packing material. The pile is aerated with an oxygen-containing gas and a liquid stream is withdrawn for the pile. A first portion of the liquid stream is returned to the pile for further contacting with the pile and a second portion of said liquid stream is taken as an acid product.

In accordance with another aspect of the invention an apparatus for producing sulfuric acid is provided. The apparatus comprises at least one reaction vessel having a base. The reaction vessel contains a bottom layer adjacent to the base. The bottom layer is comprised of a first packing material. A reactant layer is located above the bottom layer wherein the reactant layer contains a sulfur material selected from the group consisting of elemental sulfur, sulfur-containing ores, sulfide-containing ores, sulfur-containing minerals, sulfide-containing minerals and combinations thereof and an acidophilic microbe. The apparatus further comprises an aerator extending at least partially into the bottom layer. The aerator introduces an oxygen-containing gas into the bottom layer such that the oxygen-containing gas flows upward and through the reactant layer. An irrigation system extending over the reactant layer introduces an aqueous solution at or above the top of the reactant layer such that the aqueous solution flows down and through the reactant layer and into the bottom layer. During the aqueous solutions passage through the reactant layer a biological reaction takes place to produce sulfuric acid and, hence, the aqueous solution at the bottom layer is an acid solution containing sulfuric acid. A suitable means for withdrawing the acid solution from said reaction vessel is utilized and the withdrawn acid solution is split into a first and second portion. The first portion is introduced to the top of said reactant layer and the second portion is withdrawn as an acid solution product.

In the preferred embodiment, the process involves using acidophilic microbes to oxidize a variety of forms of elemental sulfur, sulfide-containing ores or minerals (i.e. pyrite and chalcopyrite), and sulfur-containing volcanic tuffs. The sulfur used in the process can be in a variety of forms. These forms may include prills, pastilles, slates, flowers, dusts, or sulfur coated onto a substrate. The pile of sulfur and/or the sulfide-containing ores or minerals can be contacted with the liquid and gas phases in a reaction vessel or a freestanding heap.

The aqueous solution, which can be distilled water, potable water, and/or an acidic or non-acidic industrial stream, is contacted with the top of solid material at either constant or intermittent rates. The primary requirement of the incoming liquid stream is that it does not contain any components that would be toxic or inhibitory to the microbial life. However, for a specific industrial application with a toxic or inhibitory component, a person skilled in the art can slowly adapt acidophilic microbes to tolerate the toxin. The oxygen-containing gas stream, preferably air, would be introduced into the pile or reactor at the appropriate rates to assure sufficient amount of oxygen for sulfuric acid production.

Also in accordance with this invention, the resulting concentration of the sulfuric acid of the subject invention can be upgraded in acid strength by a number of commercial techniques. These include, but not limited to, reverse osmosis, membrane separation, filtration, distillation, and cryogenics methodology. The waste stream from the upgraded methodology can be returned to the reaction vessel or freestanding pile keeping the entire system with zero discharge. Even at the shutdown of the plant, the remaining inoculated sulfur source can be valuable for a new plant startup. Makeup aqueous streams can be used to maintain the appropriate water balance.

DETAILED DESCRIPTION OF THE INVENTION

Figure 1:
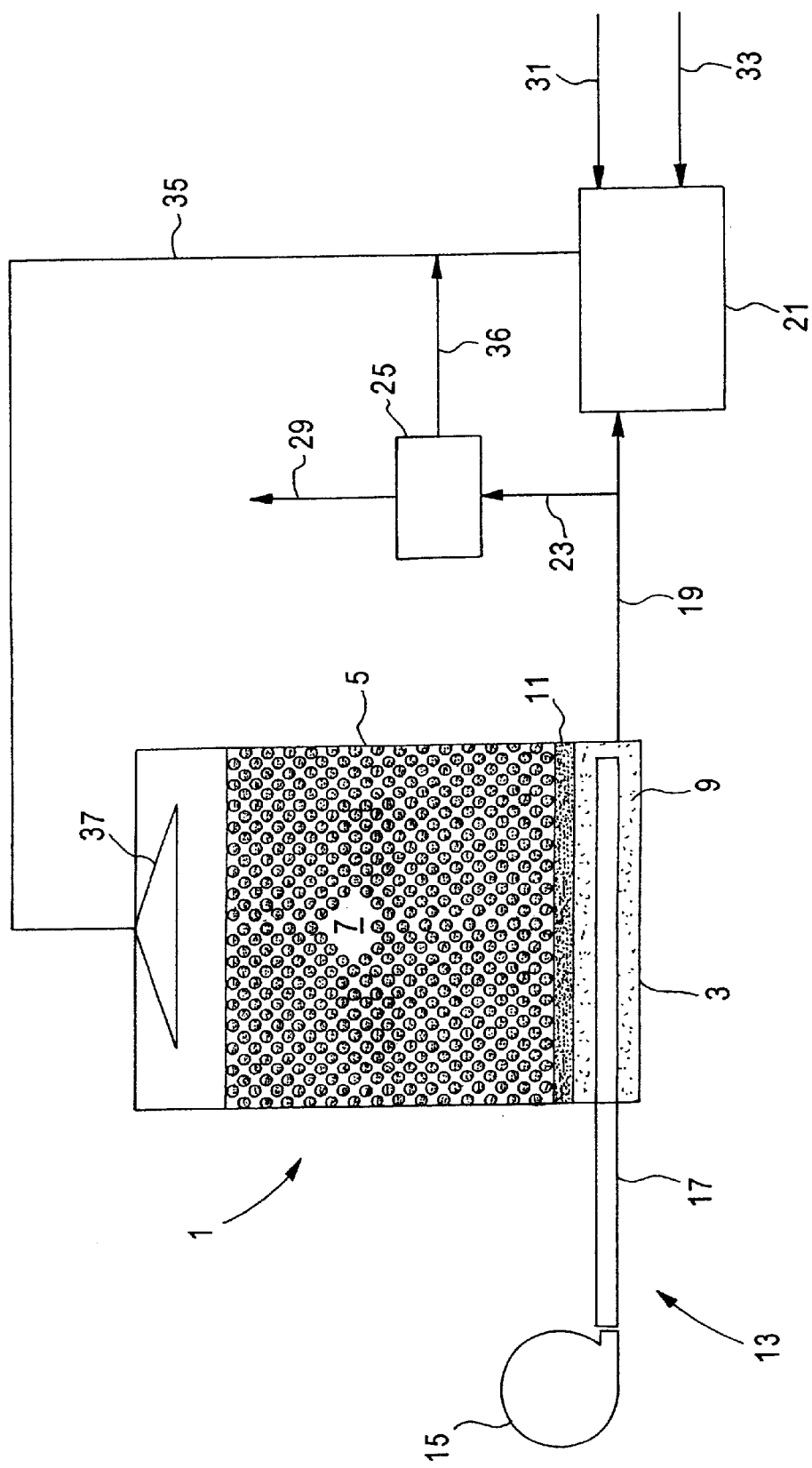
FIG. 1 is an illustration of a process in accordance with the invention for producing sulfuric acid utilizing a single reactor. The embodiment shown utilizes a trickle bed reactor.

While this invention is susceptible to embodiment in many different forms, there is shown in the drawings and will herein be described in detail some preferred embodiments of the invention with the understanding that the present disclosure is to be considered as an exemplification of the principles of the invention and is not intended to limit the broad aspect of the invention to the embodiment illustrated.

The subject invention pertains to the biological production of sulfuric acid. More particularly, the present invention pertains to the biological production of sulfuric acid in a trickle bed reaction vessel or heap type bioreactor containing elemental sulfur, sulfur-containing ores, sulfide-containing ores, sulfur-containing minerals, sulfide-containing minerals and combinations thereof (herein sometimes referred to as "sulfur material"). In the preferred embodiment, the method of the subject invention involves using oxidizing bacteria or acidophilic fungi to oxidize elemental sulfur or sulfide-containing ores or minerals (i.e. pyrite and chalcopyrite), and/or sulfur-containing volcanic tuffs to produce sulfuric acid.

One aspect of the invention pertains to advantageous methods for producing sulfuric acid from sulfur material. The sulfur material is contacted with the inoculum containing an acidophilic microbe. As used herein "acidophilic microbe" refers to a biological organism suitable for producing sulfuric acid from a sulfur material, such as *Thiobacillus thiooxidans, Thiobacillus ferooxidans,* Sulfolobus or other oxidizing bacterial species, or other acidophilic microbes such as fungi. The sulfur material is contacted with the acidophilic microbe in the presence of air and water, the sulfur in the sulfur material is oxidized by these microorganisms to sulfuric acid which is contained in the resulting aqueous solution. Preferably, the sulfur material will be contacted with the acidophilic microbes in the presence of air, water and nutrients in order to maintain the desired cell growth and sulfuric acid production. The acidophilic microbes can be obtained from a commercial culture collection or can be isolated from natural sources, for example, soil or mine water. The acidophilic microbes used can be pure strains or can be mixtures of two or more acidophilic microbes. After an equilibrium and/or an adequate acid concentration is attained, a product stream of acid solution can be removed and used directly for acidification or sent to be upgraded to a higher concentration of acid. Commercial techniques include reverse osmosis, membrane separation, filtration, distillation, and cryogenics methodology. Fresh water or other industrial aqueous streams can be added back into the system in order to maintain water balance. This process can be operated at ambient or elevated temperatures depending on the microorganisms used.

FIG. 1 shows an illustration of a preferred apparatus for practicing the invention. In FIG. 1 reactant layer or sulfur pile 7 is contained within reaction vessel 1. Vessel 1 has a bottom 3 and a circumferential side wall 5. Side wall 5 extends up from bottom 3 encompassing the sulfur pile 7. It is within the scope of the invention for the sulfur material to be in a freestanding pile or heap, that is a pile or heap not contained within a vessel, or, alternatively, the pile may be contained within a reaction vessel such as that illustrated in FIG. 1. If a free standing pile or heap is utilized, then a reaction vessel comprising a bottom or base will still be utilized under the sulfur material in order to collect the acid solution produced by the sulfur pile. Such bottom or base may have a lip or circumferential side wall of sufficient height to contain the acid solution that is being drained off. For industrial applications, which are the preferred embodiments, the pile will typically be greater than 10 m$^3$ in volume.

Sulfur pile 7 contains a sulfur material and a biological organism suitable for producing sulfuric acid ("acidophilic microbe") such as *Thiobacillus thiooxidans,* Sulfolobus or other oxidizing bacterial species, or other acidophilic microbes such as acidophilic fungi. Preferably the sulfur pile will contain a packing material. The packing material can be any material that will not be toxic to the biological organism and will provide spacing to improve aeration of the sulfur pile. Generally, the packing material will be either an inert material that is resistant to sulfuric acid or a material that will act as a substrate, provide nutrients for the acidophilic microbes and/or provide a sulfur source for the acidophilic microbes. Preferred inert packing materials are crushed glass, glass beads, polymer beads, polymer chips and polymer substrates. If a polymer is utilized for the packing material it can be polyethylene, polypropylene, or another suitable polymer that is resistant to being denatured by the sulfuric acid. Particularly preferred inert packing materials are polymer substrates that have a high surface area such as a ring and pin packing material sold under the name BIOBALLS or spherical packings having a network of ribs, struts and/or drip rods marketed under the name JAEGER TRI-PACKS. Preferred packing materials that will act as a substrate, provide nutrients for the acidophilic microbes and/or provide sulfur for the acidophilic microbes include rock, gravel, sulfur-containing ores, sulfide-containing ores, sulfur-containing minerals, sulfide-containing minerals and combinations thereof. Such ores and minerals include pyrite, chalcopyrite and volcanic tuffs. Presently, the most preferred packing material is sulfur-containing or sulfide-containing ores and minerals and combinations thereof. Generally, the packing material will make up between about 25% and about 75% of the pile by weight. It is preferred, especially in the case where the sulfur material is elemental sulfur and the packing material is sulfur-containing or sulfide-containing ores and/or minerals, that the packing material make up from 30% to 60% of the pile by weight and, more preferably, from 40% to 50% of the pile by weight.

In a specific embodiment, the sulfur can be attached to high surface area substrates such as BIOBALLS or JAEGER TRI-PACKS, using a polymer binder formulation in a drum roll or other suitable operation. The sulfur particles are placed in a vat, and water solution is pumped throughout the bed until the desired sulfuric acid production is obtained.

Returning now to FIG. 1, a layer of packing material 9 is located below reactant layer or sulfur pile 7. Layer 9 is adjacent to bottom 3 and aids in the drainage and withdraw of the acid solution produced by sulfur pile 7. Layer 9 can be any of the aforementioned packing materials. Additionally, screen 11 can be located between sulfur pile 7 and layer 9 to help prevent sulfur material from moving into layer 9.

Aerator 13, comprising an air blower or compressor 15 and a suitable means for introducing the air into the reaction vessel such as perforated pipe 17, is also provided. Perforated pipe 17 extends from air blower 15 into reaction vessel 1 at layer 9 so that the air provide enters layer 9 and flows up through sulfur pile 7. In this manner layer 9 acts as a baffle to help disperse air evenly throughout sulfur pile 7. While aerator 13 has been discussed in terms air, any oxygen-containing gas that helps promote the growth of the biological organism is suitable for use. Additionally, air blower 15 can be replaced with a compressed air cylinder or other means of forcing air into perforated pipe 17.

Acid solution is withdrawn from reaction vessel 1 through conduit 19. Conduit 19 preferably withdraws the acid solution at layer 9 in order to obtain the greatest acid concentration and to minimize the removal of sulfur from the reaction vessel. A first portion of acid solution is introduced into product reservoir 21 and a second portion is withdrawn through conduit 23.

In product reservoir 21 the first portion can be combined with replacement biological organisms and nutrients introduced through conduit 31 and/or replacement water through conduit 33 to produce a feed stream 35. Feed stream 35 is introduced into reaction vessel 1 by irrigation system 37. Irrigation system 37 comprises a sprayer or disperser in order to introduce the feed stream evenly over the surface of sulfur pile 7.

The second portion can be utilized as it is or further processed in order to increase its concentration in acid concentrator 25. Acid concentrator 25 can be any of the usual commercial techniques. These include, for example, reverse osmosis, membrane separation, filtration, distillation, cryogenic methodology or another suitable method of increasing the acid concentration. Concentrated sulfuric acid solution is removed from acid concentrator 25 via conduit 29. The aqueous solution separated from the concentrated sulfuric acid solution in acid concentrator 25 is introduced to feed stream 35 via conduit 36 before introduction of the feed stream into reaction vessel 1.

Figure 2:
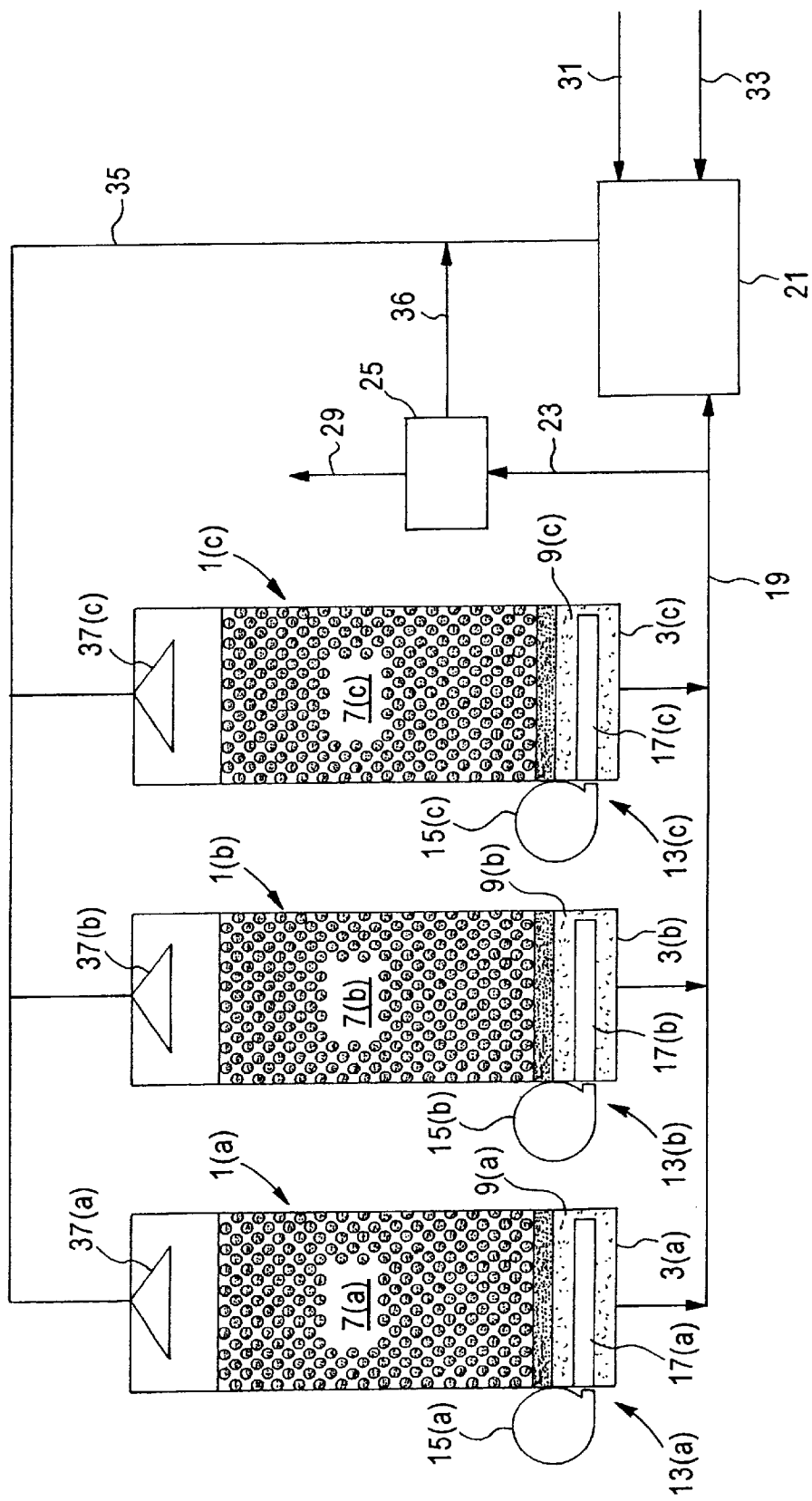
FIG. 2 is an illustration of a process in accordance with the invention for producing sulfuric acid utilizing multiple reactors.
Figure 3:
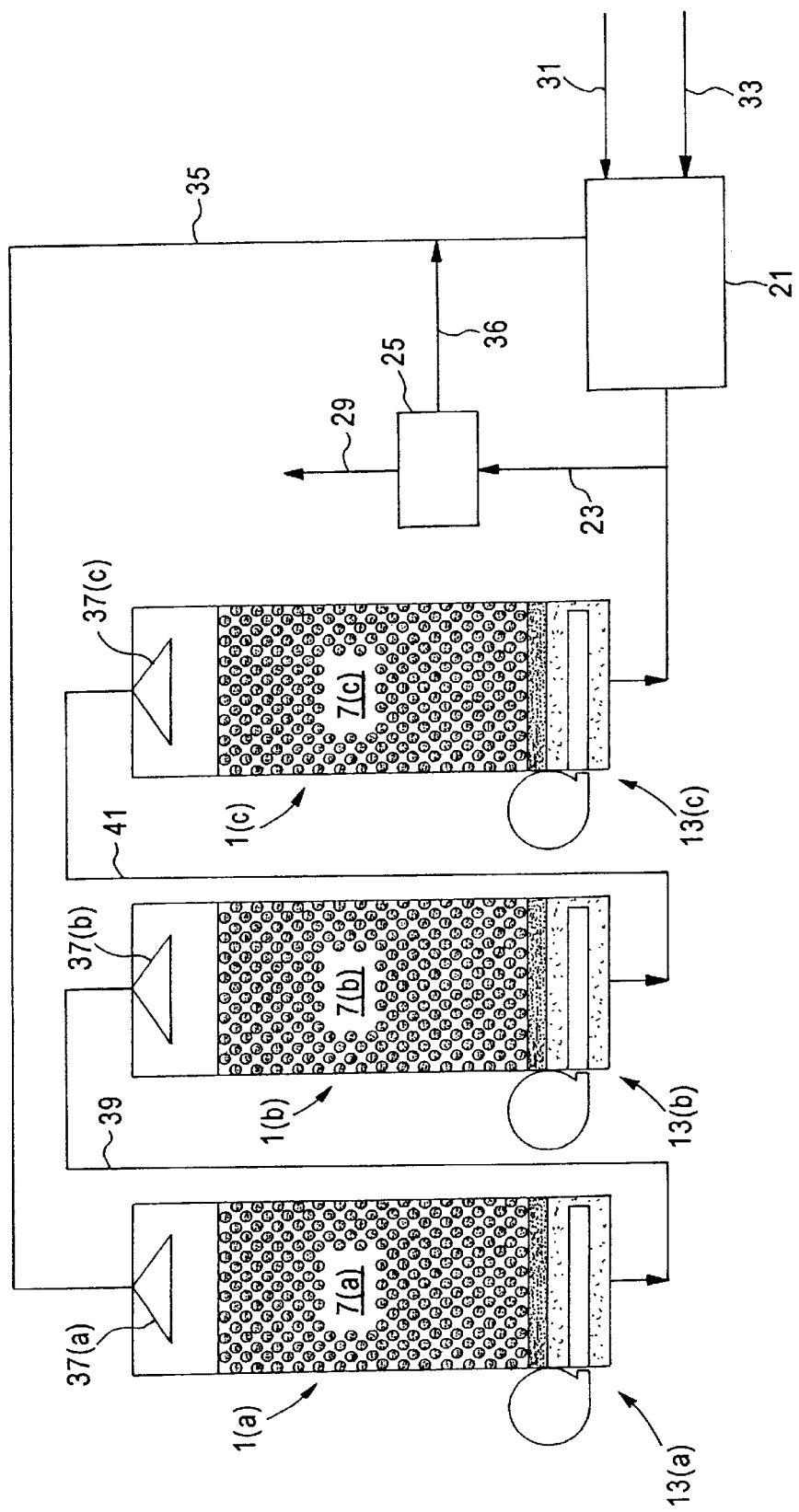
FIG. 3 is an illustration of a second embodiment of a process in accordance with the invention utilizing multiple reactors.

Turning now to FIGS. 2 and 3, other embodiments of the invention are illustrated. In FIGS. 2 and 3 like components are numbered as they were in FIG. 1. FIG. 2 illustrates an embodiment using multiple reaction vessels connected in parallel. Reaction vessels 1(*a*), 1(*b*) and 1(*c*) each have sulfur piles 7(*a*), 7(*b*) and 7(*c*); aerators 13(*a*), 13(*b*) and 13(*c*); and irrigation systems 37(*a*), 37(*b*) and 37(*c*). In the case of the aerators, each reaction vessel can have its own blower 15(*a*), 15(*b*) and 15(*c*) as illustrated or can share a common blower. The reaction vessels of FIG. 2 are connected in parallel so that the withdrawn acid solutions from the reaction vessels are combined for introduction into the product reservoir 21 and the acid concentrator 25.

FIG. 3 illustrates an embodiment using multiple reaction vessels connected in series. Accordingly, the withdrawn acid solution from reaction vessel 1(*a*) is used as the feed stream for reaction vessel 1(*b*) and is introduced to irrigation system 37(b) via line 39. Similarly, the withdrawn acid solution from reaction vessel 1(b) is used as the feed stream for reaction vessel 1(c) and is introduced to irrigation system 37(c) via line 41. The withdrawn acid solution from 1(c) is introduced to acid condenser 25 and product reservoir 21 and feed stream 35 is introduced into reaction vessel 1(a) through irrigation system 37(a).

The sulfur may be used in granular form in columns or in heaps. The sulfur material used in the inventive process can be elemental sulfur, sulfur-containing ores, sulfide-containing ores, sulfur-containing minerals, sulfide-containing minerals and combinations thereof. The elemental sulfur used in the process of the subject invention can be in a variety of forms that include prills, pastilles, slates, flowers, dusts, or sulfur coated onto a substrate. The sulfur or sulfide-containing ore or mineral are preferably selected from pyrite, chalcopyrite and volcanic tuffs. It is presently most preferred to use elemental sulfur in the form of prills, pastilles, slates and combinations thereof. It is preferred that the majority (90% or more by weight) of the sulfur material should be held on a 100 or less mesh and, more preferably on a 60 or less mesh. An additional embodiment, the sulfur can also be coated onto a high surface area substrate, such as one-inch to one and a half-inch BIOBALLS or JAEGER TRI-PACKS substrates. The high surface areas substrates are preferably polypropylene, but can be other appropriate polymeric material.

The aqueous solution, which can be, for example, distilled water, potable water, and/or an acidic or non-acidic industrial stream, is applied to the top of solid substrate at either constant or intermittent rates. The primary requirement of the incoming liquid stream is that it does not contain any components that would be toxic or inhibitory to the microbial life. However, for a specific industrial application with a toxic or inhibitory component, a person skilled in the art can slowly adapt acidophilic microbes to tolerate the toxin. Additionally, nutrients can be present in the aqueous solution or introduced into the aqueous solution to promote the growth of the biological organism and replacement biological organisms can be introduced through aqueous solution. Generally, the aqueous solution can be introduced at any suitable rate. Typically, the rate will be between about 0.5 and about 40.0 $1/min/m^2$, where $m^2$ refers to the surface area of the sulfur pile. Preferably, the rate will be between 2.0 and 21.0 $1/min/m^2$.

The oxygen-containing gas stream, preferably air, would be introduced into the solid heap or reactor at the appropriate rates to assure sufficient amount of oxygen for sulfuric acid production. The rate for introducing the oxygen-containing gas stream will vary with conditions, such as altitude, temperature and mineral content of the effluent, but typically will fall within the range of from 10 1/day/metric ton of sulfur to 1000 1/day/metric ton of sulfur.

The subject invention provides low capital cost process for sulfuric acid that can be built and operated at mines and plants located in areas lacking the infrastructure necessary to handle concentrated sulfuric acid. Most copper leaching operations use aqueous solutions of sulfuric acid that contain less than 20 g/l sulfuric acid. Current methods use concentrated sulfuric acid (~98%) that is diluted at the site to produce the desired concentration for the leach operation. The use of this process permits generation of aqueous sulfuric acid solutions very near the point of use, eliminating the hazards to personnel and the environment that are associated with the current production of sulfuric acid.

The Examples below demonstrates this process using *Thiobacilus thiooxidans;* however, any sulfur oxidizing acidophilic microorganisms may be used to produce sulfuric acid in the manner described herein. Sulfur may be present in any form that allows sufficient contact with oxygen and an aqueous solution.

The extraction of metals from sulfide concentrates or the production of sulfuric acid solution from elemental sulfur or pyrite is facilitated by the use of BIOBALLS or JAEGER TRI-PACKS substrates. However, systems described herein are not limited to the use of columns of packed only with BIOBALLS, JAEGER TRI-PACKS substrates or other column packing materials, but may also contain mixtures of various sulfur forms, sulfide-containing ores and/or minerals, volcanic tuffs, and/or non-sulfide ores.

The following are examples that illustrate procedures for practicing the invention. These examples should not be construed as limiting.

EXAMPLE 1

1.95 kg of sulfur heated to just above the temperature to become molten was spread evenly over 10.9 liter volume of 2.54 cm BIOBALLS substrates. The coated BIOBALLS substrates were placed in a 12.7 cm diameter cylindrical container containing a screen at the bottom to retain the coated materials. The cylinder was placed over the reservoir containing 4.0 liters of distilled water inoculated with acidophilic microbes and Media 125. Media 125 contains the chemicals $(NH_4)_2SO_4$, $MgSO_4.7H_2O$, $CaCl_2$, $KH_2PO_4$ and $FeSO_4$. The solution was circulated with a pump at a flow rate of 2.16 liters per minute. At the top of the coated BIOBALLS substrates the solution was evenly sprayed over the entire top surface. Daily additions of distilled water were added to maintain the reservoir volume at 4.0 liters. The aqueous solution was circulated until the acid concentration reached 20 grams per liter. At this point, the appropriate volume of aqueous solution was removed and the same amount of distilled water added to maintain an average acid concentration of 20 grams per liter. Over the next 122 days 11.4 liters of solution was removed. The total weight of acid produced during that time was 228 grams averaging 1.86 grams per day.

EXAMPLE 2

Added to a 5.1 cm diameter cylinder with a screen at the bottom, 1.3 kg of sulfur prills was added. The cylinder was placed over a reservoir containing 4.0 liters of distilled water inoculated with acidophilic microbes, distilled water and Media 125. The solution was circulated with a pump at a flow rate of 125 ml per minute to the top of the column where it was sprayed over the top of the sulfur prills. The reservoir was kept at 4.0 liter by daily addition of distilled water. After 43 days the aqueous solution was removed and replaced with fresh distilled water. After 6 days the acid concentration rose to approximately 19 g/l. Over next 146 days an average of 75 ml of effluent with an average concentration of 2.41 g/l was withdrawn daily.

EXAMPLE 3

A trickle down bioreactor constructed with a 5.1 cm diameter cylinder, perforated distribution plate on the bottom to hold the solid sulfur and one above the sulfur designed for even distribution of aqueous solution. Four sulfur materials were tested; wet sulfur prill from Devco Companies (S1), a sulfur pastille from Shell Canada (S2), polish sulfur prill from Gulf Midstream Services (S3) and wet sulfur prill from Enersul Technologies (S4). Air was introduced via a 90 degree fritted gas dispersion tube placed in the cylinder above the distribution plate. On top of the dispersion tube 1.0 kg of formed sulfur was added. The sulfur was inoculated by contacting the sulfur with 550 ml of an aqueous solution containing acidophilic microbes and introducing air through the gas dispersion tube at approximately 40 ml/min. After 72 hours, the inoculum solution was drained from the column into a reservoir and the volume increased to 2.0 liters with the addition of nutrients and a 20 g/l sulfuric acid solution in distilled water. The aqueous solution was circulated via a peristaltic pump at a rate of 40 ml/min. Air rates were maintained at approximately 40 ml/min and the volume maintained by the addition of distilled water. The following results have been observed.

| Sulfur Type | Days | Cumulative $H_2SO_4$ Produced (g) | Average Cumulative Rate (g/day) |
|---|---|---|---|
| S1 | 43 | 28.9 | 0.68 |
| S2 | 43 | 30.4 | 0.71 |
| S3 | 43 | 34.3 | 0.78 |
| S4 | 43 | 25.9 | 0.59 |

EXAMPLE 4

Seven sulfur materials were tested in this Example 4; wet sulfur prill from Devco Companies (S5), wet sulfur prill from H.J. Baker (S6), sulfur pastille from Shell Canada (S7), wet sulfur British Columbia Rail prill (S8), polish sulfur prill from Gulf Midstream Services (S9), Canadian sulfur slate (S10) and Fisher USP Sublime sulfur powder (S11).

S5–S10 were evaluated in percolator reactors. The reactors were designed with a 250 ml glass graduated cylinder and a 90 degree fritted gas dispersion tube placed in the bottom was used to screen various solid sulfur forms. This design allows minimal mechanical shearing of the formed sulfur particles. Added to the cylinder was 50 g of sulfur and 50 ml of a acidophilic microbes inoculant. Air was bubbled through the cylinder at approximately 50 ml/min. After 90 hours the inoculant solution was decanted off and 100 ml of a 20 g/l sulfuric acid solution in distilled water and 15 ml of a nutrient solution containing 1.5 mmol/l $(NH_4)_2SO_4$, 22.0 mmol/l $KH_2PO_4$, 2.0 mmol/l $MgSO_4 \cdot 7H_2O$, 2.3 mmol/l $CaCl_2$, and 0.03 mmol/l $FeSO_4 \cdot 7H_2O$ was added. Air was bubbled at approximately 50 ml/min and volume was maintained by the addition of distilled water.

Sample S11 was evaluated by adding 10 g of powdered sulfur and 50 ml of a thiooxidant inoculant to a 250 ml Erlenmeyer flask. The slurry was stirred via a magnetic stir bar for 90 hours. Added to the slurry was 50 ml of 20 g/l sulfuric acid and 5 ml of the nutrient solution stated above. Distilled water was added to maintain constant volume. The following results have been observed.

| Sulfur Type | Days | Cumulative $H_2SO_4$ Produced (g) | Average Cumulative Rate (g/day) |
|---|---|---|---|
| S5 | 57 | 3.0 | 0.041 |
| S6 | 57 | 2.8 | 0.037 |
| S7 | 57 | 3.2 | 0.045 |
| S8 | 57 | 3.2 | 0.036 |
| S9 | 57 | 3.6 | 0.035 |
| S10 | 57 | 5.0 | 0.032 |
| S11 | 25 | 4.4 | 0.129 |

After 57 days the resulting acid concentrations ranged between 35 and 50 g/l. To each of the above percolator reactor 75 ml of effluent was removed and 75 ml of the nutrient solution described above was added. The resulting acid concentration was approximately 15 g/l. Again air was bubbled through the reactor between 50 and 100 ml/min and the volume was maintained by the addition of distilled water. The following results were observed.

| Sulfur Type | Days | Cumulative $H_2SO_4$ Produced (g) | Average Cumulative Rate (g/day) |
|---|---|---|---|
| S5 | 20 | 3.4 | 0.175 |
| S6 | 20 | 3.8 | 0.196 |
| S7 | 20 | 4.1 | 0.207 |
| S8 | 20 | 3.5 | 0.175 |
| S9 | 20 | 3.0 | 0.154 |
| S10 | 13 | 2.5 | 0.191 |

After 20 days, the acid concentrations in the percolator reactors reached between 40 and 50 g/l. Again, the 75 ml of effluent was removed and this time replaced with 75 ml of distilled water. The resulting acid concentration was approximately 15 g/l. Again air was bubbled through the reactor between 50 and 100 ml/min and the volume was maintained by the addition of distilled water. The following results were observed.

| Sulfur Type | Days | Cumulative $H_2SO_4$ Produced (g) | Average Cumulative Rate (g/day) |
|---|---|---|---|
| S5 | 4 | 0.2 | 0.059 |
| S6 | 4 | 0.6 | 0.153 |
| S7 | 4 | 0.7 | 0.165 |
| S8 | 4 | 0.5 | 0.132 |
| S9 | 4 | 0.5 | 0.135 |
| S10 | 4 | 0.5 | 0.132 |

EXAMPLE 5

Potable or distilled water can be used as the liquid in the process of the subject invention. Alternatively, other liquids and industrial streams can be used. For example, on-raffinate is passed onto a copper dump leach operation to solublize the copper from the ore body. The resulting pregnant leach solution is passed through a solvent extraction train to remove the copper. The resulting off-raffinate is re-acidified with sulfuric acid to be reused as the on-raffinate. Since the raffinate is constantly recycled, the dissolved minerals that are present in the aqueous solution include calcium, aluminum, magnesium, iron and copper.

As outlined previously, 1.95 kg of sulfur, heated to just above the temperature to become molten, was spread evenly over 10.9 liter volume of 2.54 cm BIOBALLS. The coated BIOBALLS were placed in a 12.7 cm diameter cylindrical container containing a screen at the bottom to retain the coated materials. The cylinder was placed over the reservoir containing 4.0 liters of distilled water inoculated with acidophilic microbes and the Media 125. Media 125 contains the chemicals $(NH_4)_2SO_4$, $MgSO_4 \cdot H_2O$, $CaCl_2$, $KH_2PO_4$ and $FeSO_4$. The solution was circulated with a pump at a flow rate of 2.16 liters per minute. At the top of the coated BIOBALLS the solution was evenly sprayed over the entire top surface. Daily additions of distilled water were added to maintain the reservoir volume at 4.0 liters. After three days, 2.0 liter of the initial inoculum was withdrawn and replaced with raffinate. Within 60 days, the circulating acidic solution had increased to 50 gram per liter. At this point, the appropriate volume of aqueous solution was removed and the same amount of distilled water added to maintain an average acid concentration of 50 grams per liter. Over the next 25 days 1.75 liters of solution was removed. The total weight of acid produced during that time was 35 grams averaging 1.4 grams per day.

EXAMPLE 6

As described previously, a trickle down bioreactor constructed with a 5.1 cm diameter cylinder, perforated distribution plate on the bottom to hold the solid sulfur and one above the sulfur designed for even distribution of aqueous solution. Air was introduced via a 90 degree fritted gas dispersion tube placed in the cylinder above the distribution plate. On top of the dispersion tube 1.0 kg of sulfur pastels was added. The sulfur was inoculated by contacting the sulfur for 24 hours with 600 ml of an aqueous solution containing acidophilic microbes. The inoculum solution was drained from the column into a reservoir and the volume increased to 1.0 liters with the addition of 0.4 liters of industrial off-raffinate. The aqueous solution was circulated via a peristaltic pump at a rate of 40 ml/min. Air rates have been maintained at approximately 40 ml/min and the volume maintained by the addition of distilled water. Over a period of 54 days the 42 g of sulfuric acid was produced at a rate of 0.8 grams per day.

EXAMPLE 7

The process can be used on sulfur in a non-acid-consuming host ore. A 200 gram sample of volcanic tuft containing 13% sulfur in a volcanic tuft host rock was placed into a 5 cm cylinder with a screen at the bottom to retain the ore. The cylinder was placed over the reservoir containing 0.80 liters of acidophilic microbes inoculated distilled water containing Media 125. This solution contained 0.49 g/l of free acid. The solution was pumped to the top of the cylinder at 16 ml per minute where it was sprayed over the top of the ore. The reservoir was kept at 0.80 liter by daily addition of water. After 29 days the reservoir had reached an acid content of 2.1 g/l. Over the next 11 days an average of 0.32 liters of solution was removed producing 3.5 g of sulfuric acid.

The above examples illustrate that sulfuric acid has been successfully produced using the various sulfur materials, packing materials and aqueous solutions of the invention.

As described for the inventive process and apparatus above, the leaching of elemental sulfur to produce sulfuric acid is a non-polluting bio-process. It is applicable in all parts of the world with proper application and may be used with a minimal amount of equipment. This process facilitates the production of sulfuric acid without the use of expensive capital equipment and, if properly used, creates no pollution. Conversely, current technology utilizing the burning of elemental sulfur and the processing of the resulting gases containing sulfur dioxide through catalyst beds creates air pollution and requires enormous capital expenditures.

Therefore, the process of the subject invention provides low cost sulfuric acid for mines and plants located in remote areas and in countries lacking the infrastructure necessary to handle the extremely dangerous concentrated sulfuric acid. Most leaching operations use aqueous solutions of sulfuric acid that contain less than 20 grams per liter of sulfuric acid. With current technology, sulfuric acid is made in very concentrated form and then shipped to the point of use where it is diluted with water to produce the aqueous solutions used in most leaching operations. Use of the process of the subject invention permits generation of aqueous sulfuric acid solutions very near the point of use, eliminating the hazards to personnel and the environment that are associated with the current production of sulfuric acid. Pyrite may be substituted for elemental sulfur; however, an iron removal step may be required if upgrading of the acid is desired.

It should be understood that the examples and embodiments described herein are for illustrative purposes only, and that various modifications or changes in light thereof will be suggested to persons skilled in the art and are to be included within the spirit and purview of this application and the scope of the appended claims.

That which is claimed is:

1. A process for producing sulfuric acid comprising:
   (a) contacting an aqueous solution with a sulfur material in a pile,
      (i) wherein said sulfur material is selected from the group consisting of elemental sulfur, sulfur-containing ores, sulfide-containing ores, sulfur-containing minerals, sulfide-containing minerals and combinations thereof, and
      (ii) wherein said pile additionally contains acidophilic microbes;
   (b) aerating the pile with an oxygen-containing gas;
   (c) withdrawing a liquid stream from said pile;
   (d) returning a first portion of said liquid stream to said pile for further contacting with said pile; and
   (e) taking a second portion of said liquid stream as an acid product.

2. The process of claim 1 wherein said sulfur material is elemental sulfur and is in a form selected from the group consisting of prills, pastilles, slates, dusts, powders, crystals and combinations thereof.

3. The process of claim 2 wherein said elemental sulfur is selected from the group consisting of prills, pastilles, slates and combinations thereof.

4. The process of claim 3 wherein said pile further comprises a packing material.

5. The process of claim 4 wherein said packing material is selected from the group consisting of sulfur-containing ores, sulfide-containing ores, sulfur-containing minerals, sulfide-containing minerals and combinations thereof.

6. The process of claim 5 wherein said packing material comprises between about 25% and about 75% of said pile by weight.

7. The process of claim 5 wherein said packing material comprises from 30% to 60% of the pile by weight.

8. The process of claim 5 wherein said packing material comprises from 40% to 50% of said pile by weight.

9. The method of claim 4 wherein said packing material is selected from the group consisting of crushed glass, glass beads, polymer beads, polymer chips and polymer substrates.

10. The method of claim 9 wherein said sulfur material is agglomerated onto the packing material.

11. The method of claim 9 wherein the sulfur material is coated onto the packing material.

12. The method of claim 1 further comprising the step of:
   (f) increasing the concentration of sulfuric acid in said acid product.

13. The method of claim 12 wherein said step of increasing the concentration of sulfuric acid is a method selected from the group consisting of reverse osmosis, membrane separation, filtration, distillation, and cryogenic methods.

14. The method of claim 1 wherein said aqueous solution is introduced into said pile at a rate between about 0.5 and about 40.0 1/min/m$^2$.

15. The method of claim 12 wherein said a aqueous solution is introduced into said pile at a rate between 2.0 and 21.0 1/min/m$^2$.

16. The method of claim 1 wherein said aqueous solution is contacted with said sulfur material by trickling said solution on the top of said pile and allowing said aqueous solution to flow down and through said pile.

17. A process for producing sulfuric acid comprising the step of:
   (a) contacting an aqueous solution with elemental sulfur contained in a reaction vessel by
      (i) trickling said aqueous solution on the top of said pile at a rate between 2.0 and 21.0 L/min/m$^2$ and
      (ii) allowing said aqueous solution to flow down through said elemental sulfur
   wherein said elemental sulfur is selected from prills, pastilles, slates and combinations thereof, and
   wherein said reaction vessel additionally contains acidophilic microbes and a packing material,
   wherein said packing material makes up from 30% to 60% of the reaction vessel contents by weight;
   (b) aerating the pile with an oxygen-containing gas;
   (c) withdrawing a liquid stream from said pile;
   (d) returning a first portion of said liquid stream to said pile for further contacting with said pile;
   (e) taking a second portion of said liquid stream as an acid product and
   (f) increasing the concentration of sulfuric acid in said acid product, wherein said step of increasing the concentration of sulfuric acid is a method selected from the group consisting of reverse osmosis, membrane separation, filtration, distillation, and cryogenic methods.

18. The method of claim 17 wherein said packing material is selected from the group consisting of sulfur-containing ores, sulfide-containing ores, sulfur-containing minerals, sulfide-containing minerals and combinations thereof.

19. The method of claim 17 wherein said elemental sulfur is agglomerated onto the packing material.

20. The method of claim 18 wherein said elemental sulfur material is coated onto the packing material.

* * * * *